US011156593B2

(12) United States Patent
Ghods et al.

(10) Patent No.: US 11,156,593 B2
(45) Date of Patent: Oct. 26, 2021

(54) EMBEDDED WIRELESS MONITORING SENSORS

(71) Applicant: GIATEC SCIENTIFIC INC., Nepean (CA)

(72) Inventors: Pouria Ghods, Gloucester (CA); Rouhollah Alizadeh, Nepean (CA); Mustafa Salehi, Nepean (CA); Sarah De Carufel, Ottawa (CA)

(73) Assignee: Giatec Scientific Inc., Nepean (CA)

( * ) Notice: Subject to any disclaimer, the term of this patent is extended or adjusted under 35 U.S.C. 154(b) by 122 days.

(21) Appl. No.: 16/385,205

(22) Filed: Apr. 16, 2019

(65) Prior Publication Data

US 2019/0242868 A1 Aug. 8, 2019

Related U.S. Application Data

(63) Continuation of application No. 15/474,175, filed on Mar. 30, 2017, now Pat. No. 10,324,078.

(Continued)

(51) Int. Cl.
| | |
|---|---|
| *G01N 33/38* | (2006.01) |
| *B28C 7/02* | (2006.01) |
| *C04B 40/00* | (2006.01) |
| *B28B 23/00* | (2006.01) |
| *G01N 17/04* | (2006.01) |
| *G01N 27/04* | (2006.01) |

(52) U.S. Cl.
CPC ....... *G01N 33/383* (2013.01); *B28B 23/0031* (2013.01); *B28C 7/02* (2013.01); *C04B 40/0096* (2013.01); *G01N 17/04* (2013.01); *G01N 27/048* (2013.01); *G01N 2203/0092* (2013.01)

(58) Field of Classification Search
CPC .................................................... B28C 7/024
See application file for complete search history.

(56) References Cited

U.S. PATENT DOCUMENTS

| | | | |
|---|---|---|---|
| 2004/0153270 A1* | 8/2004 | Yamashita | G01N 33/383 |
| | | | 702/81 |
| 2010/0098353 A1* | 4/2010 | Mountain | E02D 15/06 |
| | | | 383/1 |

OTHER PUBLICATIONS

Stackelberg et al., Physical nature of linear correlations "strength-resistivity" by control hardening cement compositions, Building Materials, 2010, 3, pp. 118-122 (Year: 2010).*

(Continued)

*Primary Examiner* — Matthew G Marini
(74) *Attorney, Agent, or Firm* — Rosenberg, Klein & Lee

(57) ABSTRACT

Concrete can be one of the most durable building materials where consumption is projected to reach approximately 40 billion tons in 2017 alone. Despite this the testing of concrete at all stages of its life cycle is still in its infancy although testing for corrosion is well established. Further many of the tests today are time consuming, expensive, and provide results only after it has been poured and set. Accordingly, by exploiting self-contained wireless sensor devices, which are deployed with the wet concrete, the in-situ curing and maturity measurement data can be established and employed together with batch specific concrete data to provide rapid initial tests and evolving performance data regarding the concrete cure, performance, corrosion of concrete at different points in its life cycle. Such sensors remove subjectivity, allow for rapid assessment, are integrable to the construction process, and provided full life cycle assessment.

21 Claims, 10 Drawing Sheets

Related U.S. Application Data

(60) Provisional application No. 62/315,202, filed on Mar. 30, 2016.

(56) References Cited

OTHER PUBLICATIONS

Mauricio Mancio, Jeffrey R. Moore, Zenzile Brooks, Paulo J. M. Monteiro, Steven D. Glaser, Instantaneous In-Situ Determination of Water-Cement Ratio of Fresh Concrete, ACI Materials Journal, 107(6) (Year: 2010).*

Lian-zhen XiaoZong-jin LiXiao-sheng Wei, Selection of superplasticizer in concrete mix design by measuring the early electrical resistivities of pastes, Cement & Concrete Composites (2007) 350-356 (Year: 2007).*

* cited by examiner

EMBEDDED WIRELESS MONITORING SENSORS

CROSS-REFERENCE TO RELATED APPLICATIONS

This patent application claims the benefit of priority from U.S. patent application Ser. No. 15/474,175 filed Mar. 30, 2017 entitled "Embedded Wireless Monitoring Sensors" which itself claims priority from U.S. Provisional Patent Application 62/315,202 filed Mar. 30, 2016 entitled "Embedded Wireless Monitoring Sensors", the entire contents of which are incorporated herein by reference.

FIELD OF THE INVENTION

The present invention relates to process monitoring and more particularly to compact self-contained electrical sensors with wireless interfaces.

BACKGROUND OF THE INVENTION

Concrete can be one of the most durable building materials and structures made of concrete can have a long service life. Concrete is a composite construction material composed primarily of aggregate, cement, and water. Further, as it is used as liquid that subsequently hardens it can be formed into complex geometries and may poured either directly into formworks at the construction site. For large construction projects contractors order pre-mixed concrete, known as ready mix concrete, and this dominates sales with approximately 70% of the U.S cement use in 2014. However, approximately 4% of the U.S. cement sales in 2014 were through building materials dealers such as national chains such as Home Depot™, Lowes™, Payless Cashway™ etc. to local and regional building material suppliers. With a total U.S. cement market in 2014 of approximately 90 million metric tons this represents 3.6 million metric tons of cement sold in a range of bag sizes from 20 kg to just over 40 kg. Assuming 33.3 kg average bag weight this represents the equivalent of 30 bags per ton or approximately 110 million bags of cement. In addition to these cement sales there were also additional sales of bagged concrete and mortar on top of these figures.

These are used in a wide range of projects including residential and commercial structures subject to planning permission and other municipal/state/national requirements. However, whilst quality controls are applied by the manufacturers and constructors with ready mix concrete no such controls are generally applied when bag cement is used. This arises as, whilst testing techniques for concrete have evolved and will continue to evolve to meet requirements for faster construction, shorter durations of formwork use, and cost reductions, many of these techniques require samples be taken, fully extended curing of the concrete achieved and laboratory measurements/testing performed. Typically, even the simple mechanical tests such as the slump test are not performed on site.

Accordingly, it would be beneficial to provide building owners, insurers, contractors, regulatory authorities, architects, and others with data regarding the cure and performance of concrete made on site with bagged cement or bagged concrete mixes. It would be further beneficial for the necessary measurements and calculations to be automatically performed with a self-contained data acquisition/logging module added to the concrete which wirelessly communicates to a portable electronic device during installation and/or during lifetime of the concrete structure formed.

It would be further beneficial for such automated testing/characterization using self-contained data acquisition/logging modules to be employed/compatible with other products during their manufacturing, deployment and lifetime.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to address limitations within the prior art relating to process monitoring and more particularly to compact self-contained electrical sensors with wireless interfaces.

In accordance with an embodiment of the invention there is provided a method comprising:
storing data relating to properties of a first material within which a self-contained sensor device is to be disposed within the self-contained sensor device;
shipping the self-contained sensor device in association with either a second material for use in forming a mixture of the first material or the mixture of the first material;
deploying the self-contained sensor device in association with the mixture of the first material;
performing at least a measurement of a plurality of measurements upon the mixture of the first material with the self-contained sensor; and
determining based upon at least the measurement obtained with the self-contained sensor device a characteristic of the first material.

In accordance with the embodiment of the invention for the method the self-contained sensor device comprises:
a first predetermined portion of the construction material system comprising a first predetermined portion of a first material; and
a second predetermined portion of the construction material system comprising at least one self-contained sensor device of a plurality of self-contained sensor devices, each self-contained sensor device for performing at least one measurement of a plurality of measurements upon the first material; wherein
the first predetermined portion of the construction material system and the second predetermined portion of the construction material system are intended to be shipped to a predetermined location for deployment as part of a construction project.

In accordance with an embodiment of the invention there is method of establishing maturity data relating to a material being cured comprising:
establishing the electrical resistivity ($\rho_t$) of the material at a plurality of specific times (t);
establishing the in-situ compressive strength ($S_t$) of the material at the plurality of specific times;
deriving c and d using $S_t = c + d \cdot \log(\rho_t)$;
substituting c and d into $$\frac{(a-c)}{d} = X_1 \text{ and } \frac{b}{d} = X_2$$

wherein $X_1$ and $X_2$ are coefficients obtained from regression analysis; and substituting into S=a+b·log(M) to derive a prediction of the mature compressive strength M.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

The present invention is directed to process monitoring and more particularly to compact self-contained electrical sensors with wireless interfaces.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A "portable electronic device" (PED) as used herein and throughout this disclosure, refers to a wireless device that requires a battery or other independent form of energy for power. This includes devices including, but not limited to, cellular telephone, smartphone, smart watch, personal digital assistant (PDA), portable computer, pager, portable multimedia player, portable gaming console, laptop computer, tablet computer, and an electronic reader.

A "fixed electronic device" (FED) as used herein and throughout this disclosure, refers to a wired and/or wireless device used which is dependent upon a form of energy for power provided through a fixed network, e.g. an electrical mains outlet coupled to an electrical utilities network. This includes devices including, but not limited to, portable computer, desktop computer, computer server, Internet enabled display, mainframe, sensor hub and server cluster. Such PEDs and FEDs supporting one or more functions and/or applications including, but not limited to, data acquisition, data storage, data analysis, communications, and Internet/Web interface.

A: Smart Rocks and Smart Concrete

In order to address the issues identified within the background supra the inventors have established a methodology exploiting "embedded sensors" or what the inventors refer to as "SMArt rocKs" (SMAKs) and "Smart Concrete" which refers to concrete with SMAK(s) within or in contact with the concrete.

Figure 1:
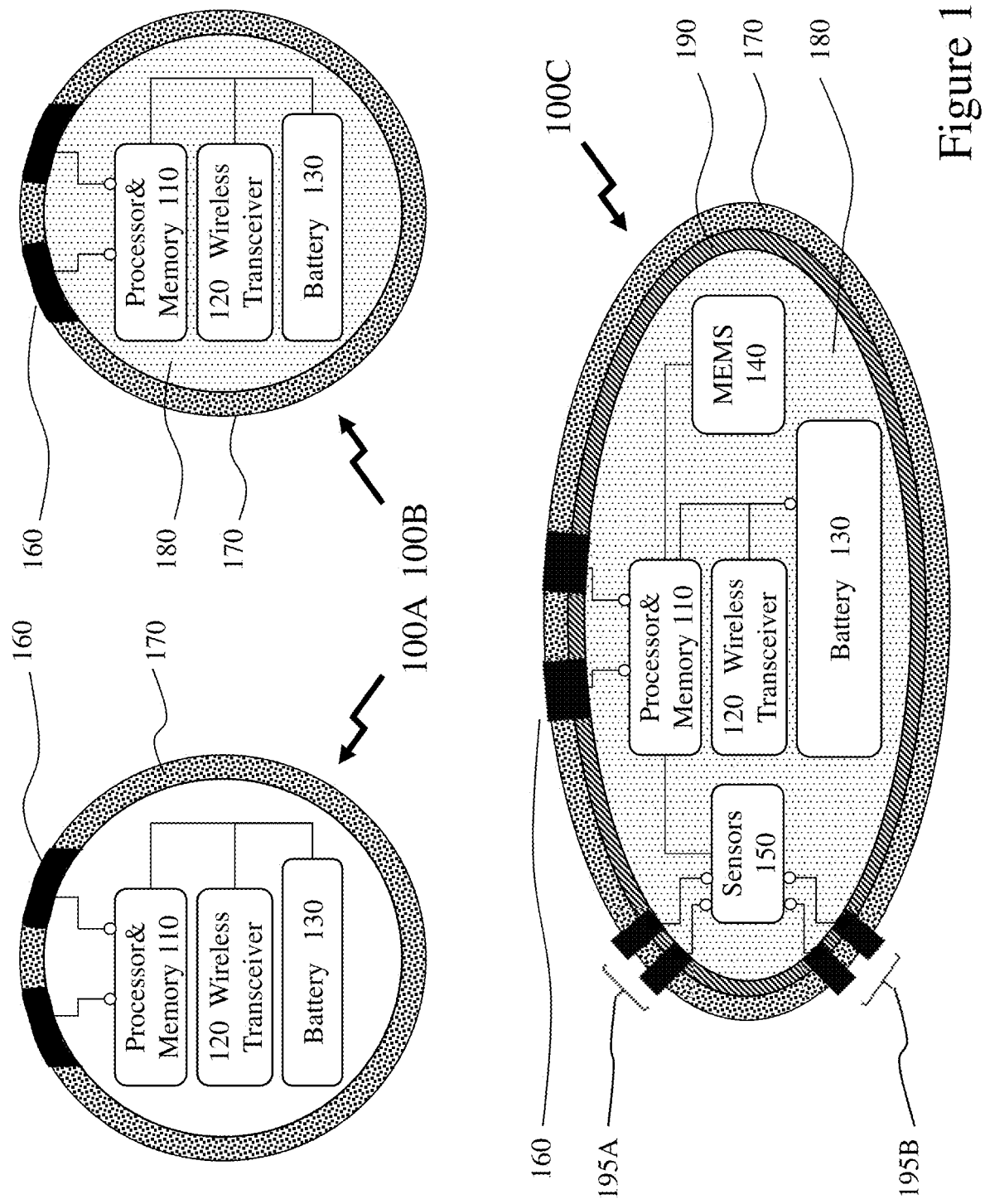
FIG. 1 depicts examples of concrete infrastructure that require characterization as well as rebar reinforced concrete.

Referring to FIG. 1 there are depicted first to third SMAKs 100A to 100C according to embodiments of the invention. Referring to first SMAK 100A contacts 160 are formed within outer shell 170 defining an interior within which are disposed a processor with associated memory 110 (hereinafter, processor). The processor 110 being coupled to a wireless transceiver 120 and a battery 130. Accordingly, electrical conductivity (for example) between the contacts 160 may be monitored (e.g. arising from water within a concrete mix), processed with the processor 110, stored and then subsequently transmitted via wireless transceiver 120 when a link is established to a portable electronic device (PED) such as smartphone, tablet PC, or dedicated device. The shell 170 may be formed from a variety of materials, including but not limited to, metals (from which the contacts are isolated by insulating rings etc.), ceramics (e.g. alumina, zirconia, etc.), composites (e.g. fiber reinforced polymer, ceramic matrix composites, concrete, glass-reinforced plastic) and plastics (e.g. short-fiber thermoplastics, long-fiber thermoplastics, thermosetting plastics, filled plastics, synthetic rubber, elastomer, etc.).

Second SMAK 100B depicts essentially the same construction as SMAK 100A except that the interior of the shell is now filled with a filler 180. Second filler material 180 may be a resilient filler 180 surrounded by a soft shell 170 such as synthetic rubber or elastomer, for example, or alternatively the filler 180 may be semi-resilient in combination with a resilient shell 170. Such semi-resilient fillers 180 may include thermosetting resins, catalyzed resins, cured silicone gels, etc. used in conjunction with a shell 170 formed from a plastic or rubber, for example.

Third SMAK 100C exploits the same filler 180 with shell 170 but now an intermediate casing 190 is disposed between the outer shell 170 and the inner filler 180. For example, casing 190 may be an impermeable membrane, e.g. Gore-Tex™, that limits moisture ingress to the SMAK 100C but allows air or gas permeability. Further, SMAK 100C now comprises in addition to the processor 110, wireless transceiver 120, and battery 130 additional sensors 160 which are coupled to first and second SENsor INTerfaces (SENINTs) 190A and 190B which together with contacts 160 provide external sensing data to the processor 110. Further a microelectromechanical system (MEMS) 140 within the SMAK 100C provides data to the processor 110 wherein the MEMS 140 may comprise, for example, an accelerometer such as a one-dimensional (1D), two-dimensional (2D) or three-dimensional (3D) accelerometer providing data relating to motion, shock, etc. Within different embodiments of the invention some SENSINTs may have direct exposure to the external environment whereas others may be indirect or via a barrier material etc. or have a characteristic that varies in response to an external environmental aspect. Sensors may include, but are not limited to, temperature, electrical resistance, pressure, light, acceleration (e.g. MEMS accelerometer), vibration (e.g. MEMS sensor), humidity (e.g. capacitive sensor barriered with a vapour barrier to prevent direct fluid contact), pH (e.g. ion sensitive field effect transistor—ISFET pH sensor), ion content (to detect externally penetrating chemicals or materials), chloride content, microphone or acoustic sensor (to detect crack propagation), gas sensor (e.g. nitrogen, oxygen to detect air within cracks propagating to the surface of the concrete), corrosion detectors, visible optical sensors, ultraviolet optical sensors, and infrared optical sensors. More advanced sensors may provide dedicated hardware, functionality, and software to enable more advanced techniques such as nuclear magnetic resonance, electrochemical, X-ray diffraction, optical spectrometry, thermogravimetric analysis, a half cell, etc. as well as corrosion resistance etc.

Figure 2:
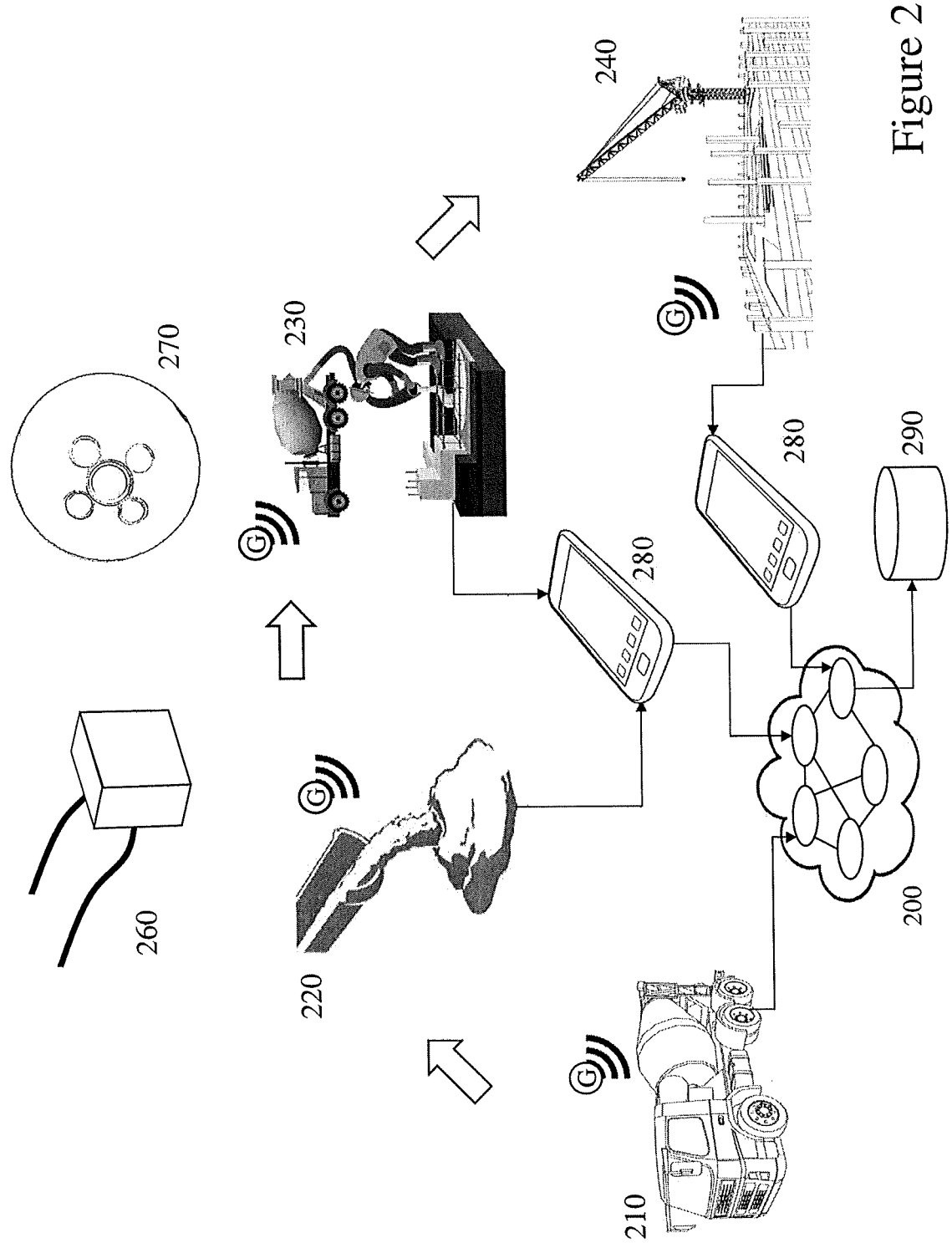
FIG. 2 depicts an embedded sensor methodology for data logging concrete properties from initial mix through pouring, curing, and subsequently according to an embodiment of the invention.

As such SMAKs, such as first to third SMAKs 100A to 100C, depicted in prototype 260 and production concept form 270 in FIG. 2, may be added to a concrete batch loaded onto a concrete truck at the batching plant, within an embodiment of the invention. It is therefore possible to "tag", i.e. load into, the SMAK information relevant to the mix as well as delivery data etc. This information as well as other measurements made by the SMAKs during the transportation, pouring, and placement can be accessed by wireless interface by the end user once the concrete is delivered to the construction site, as it is poured, and during its curing, maturation processes.

As such the tagging of the SMAKs may include, but not be limited to, information such as batch identity, truck identity, date, time, location, batch mix parameters, etc. but also importantly information such as the maturity calibration curves for the mix established by the manufacturer. Accordingly, depending upon the degree of complexity embedded into the SMAK such data may be either retrieved for remote storage and subsequent use or it may be part of the SMAKs processing of electrical measurement data such that calibration data of the concrete mix is already factored into the data provided by the SMAKs. Accordingly, the SMAKs, such as prototype 260 and production concept form 270 may be added to the concrete at the batching point 210 either tagged already or tagged during loading. Subsequently upon delivery and pouring 220 the SMAKs may be read for information regarding the delivery process etc.

Once poured the SMAKs may be read for curing information 230 and then subsequently, depending upon the battery—power consumption etc., periodically read for lifetime data 240 of the concrete. In each instance the acquired data may be acquired wirelessly and stored on a user's PED or it may then be pushed to a network 200 and therein to one or more servers 290. For devices wireless interrogating the SMAKs these may be executing a software application which presents to the user concrete parameter data either as provided from the SMAK(s) directly using the calibration curves stored within or upon the device using calibration curve data stored within the SMAK but not processed by it, stored within the device or retrieved from the data stored upon the remote server 290.

As depicted prototype sensor 260 is enabled when an electrical circuit is completed via the flying leads. In production concept form 270 the sensor may be enabled through a wireless signal, a vibration exceeding a threshold, via an electrical circuit being completed, increase in humidity beyond a threshold, decrease in light, etc. Accordingly, the embodiments of the invention support tagging the sensors and embedding the maturity calibration curves in the sensor. These curves are mix-specific and depending on the temperature history of the concrete can be used to estimate the strength of concrete. By embedded them within the sensors and the sensors employing this data the concrete manufacturer does not need to release commercially sensitive information such as their proprietary mix and calibration curves.

Based upon the combination of SMAKs within the concrete mix and their wireless interrogation and mobile/cloud based software applications other technical enhancements may be implemented, including for example:

Weather forecast API, such that the ambient temperature prediction in conjunction with current concrete data can be used to predict/project the strength identifying quality problems earlier;

Automatic detection of concrete pouring time, e.g. from electrical connection once the concrete is poured or change in the pressure, humidity, light etc.;

Tagging the sensor using NFC with smartphone;

Data integrity and management on remote servers;

Data analytics and/or artificial intelligence on data analysis as the SMAK manufacturer may acquire data from a large number of job sites allowing additional analytics, reporting, alarms etc.;

A SMAK manufacturer may establish so-called "big data" on concrete properties and concrete curing cycles/processes across a large number of job sites, geographic regions, time frames etc. allowing them to provide feedback from their server based processes to the end user;

Push notifications, such as for example the formwork company is notified when is the time to remove the formwork based upon actual concrete curing data; and Heat optimization wherein for example closed loop feedback of the temperature history and strength development can be employed to optimize heating employed in cold climates to ensure the concrete slabs gain sufficient strength within a specific period.

Considering heat optimization then this may also be used in establishing closed-loop feedback to optimize cooling of "mass concrete". "Mass concrete" is defined by the American Concrete Institute as "any volume of concrete with dimensions large enough to require that measures be taken to cope with the generation of heat from hydration of cement and attendant volume change to minimize cracking." Accordingly, cooling water is typically passed through pipes embedded in the mass concrete in order to keep the temperature gradient between the surface and the core of concrete below a threshold. Accordingly, SMAK sensors distributed within the mass concrete would allow for this process to be controlled, adjusted, measured, verified and optimized.

In addition to measuring, for example, temperature, DC electrical conductivity, and AC electrical conductivity it would be evident that additional parameters as discussed and described supra in respect of embodiments of the invention may be measured and monitored, including, but not limited to, concrete moisture content, concrete internal relative humidity, concrete pH, concrete mixture consistency, concrete workability (slump), concrete air content, hydraulic pressure, segregation, cracking, penetration of external ions into concrete, dispersion of fibers, and dispersion of chemical additives and supplementary cementitious materials.

Figure 3:
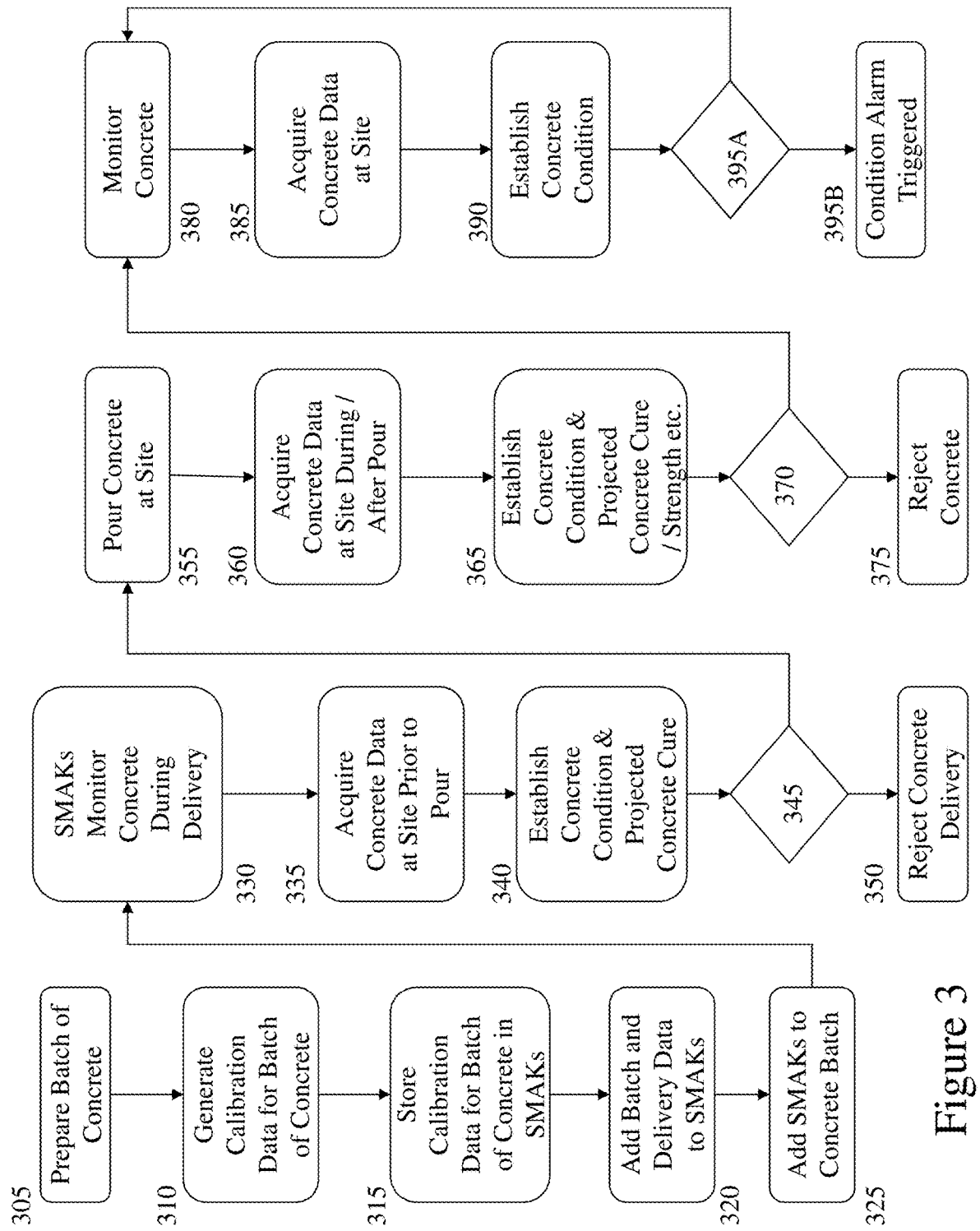
FIG. 3 depicts an exemplary process flow for an embedded sensor methodology for data logging concrete properties for concrete delivered to a worksite from initial mix through pouring, curing, and subsequently according to an embodiment of the invention.

Now referring to FIG. 3 there is depicted an exemplary flow for SMAK methodology for data logging concrete properties from initial mix through pouring, curing, and subsequently according to an embodiment of the invention. Accordingly, the process begins with step 305 wherein a batch of concrete is prepared wherein in step 310 the calibration data, for example the maturity calibration curves, is generated for that batch. Next in step 315 this calibration data is stored within a batch of sensors which will be embedded with the concrete mix. Subsequently, in step 320 additional data such as date, time, location, delivery identity, order data, manufacturer identity, etc. Once the sensors have been embedded with the data then they are mixed/embedded into the concrete for delivery.

Accordingly, the now SMAKs monitor the concrete during the delivery-transportation sequence in step 330 wherein at the site the current data is retrieved from the SMAKs in step 335 wherein this is employed to establish current concrete condition and projected cure in step 340 wherein a delivery accept/reject decision is made in step 345 wherein a rejection leads to step 350 otherwise the process proceeds to step 355 wherein the concrete is poured on site and the SMAKs continue monitoring. Next in step 360 the data from the sensors is retrieved either in a single retrieval event or multiple events such that in step 365 the concrete condition, projected cure, projected strength, etc. are established. Next in step 370 a decision on the concrete pour is made as to whether it will be allowed to continue curing or whether there is a problem and remedial work/tear-down etc. are required at which the process proceeds to step 375 and terminates or proceeds to step 380.

In step 380 the SMAKs continue monitoring the concrete but now for longer term characteristics as the cure has been passed at step 370. Subsequently the SMAK data is acquired in step 385 and used in step 390 to establish the concrete's condition. If everything is within defined boundaries, then the process proceeds from a decision step 395A to loop otherwise it proceeds to step 395B and an alarm is triggered with respect to the condition of the concrete. In this manner the life cycle of the concrete can be tracked with the SMAKs.

Optionally, rather than pouring the SMAKs with the concrete or pre-installing them on the rebar or within the formwork they may be installed post-pour by pushing them into the concrete once it has been poured. Within other embodiments of the invention the SMAKs may be deployed through a hose and pneumatically projected at high velocity onto a surface, so-called shotcrete.

Optionally, to provide extended lifetime of the SMAKs their initial sampling rate during activation, transport, pour and curing may be amended to an increased period between sampling points wherein, for example, after a first predetermined period (e.g. 1 week) the sampling drops to a lower rate, then again at predetermined points either time based or concrete cure derived such that, for example, sampling drops to hourly, daily etc. to provide extended battery life. Alternatively, the SMAKs may be designed for specific short life cycle for the initial portion of the concrete life cycle after which the SMAK may be read periodically, where near the surface of the structure, such as through wireless power activation as employed in Radio Frequency IDentification devices (RFID) or another wireless power transfer methodology such as HIghly RESonant WIreless POwer (HIRES-WIPO) transfer, for example, that may increase the depth at which SMAKs may be wirelessly activated.

Accordingly, data regarding the curing of a concrete structure throughout its structure may be derived rather than from a limited number of sampling points or concrete tests on delivered concrete. For example, the number of SMAKs may be established as 1 per cubic meter, 1 per 2 cubic meter, 1 per 8 cubic meter, 4 per truck irrespective of load, etc. The number may be varied in accordance with concrete mix, architect schedule so that sensitive load bearing structures are more accurately plotted than others.

Figure 4:
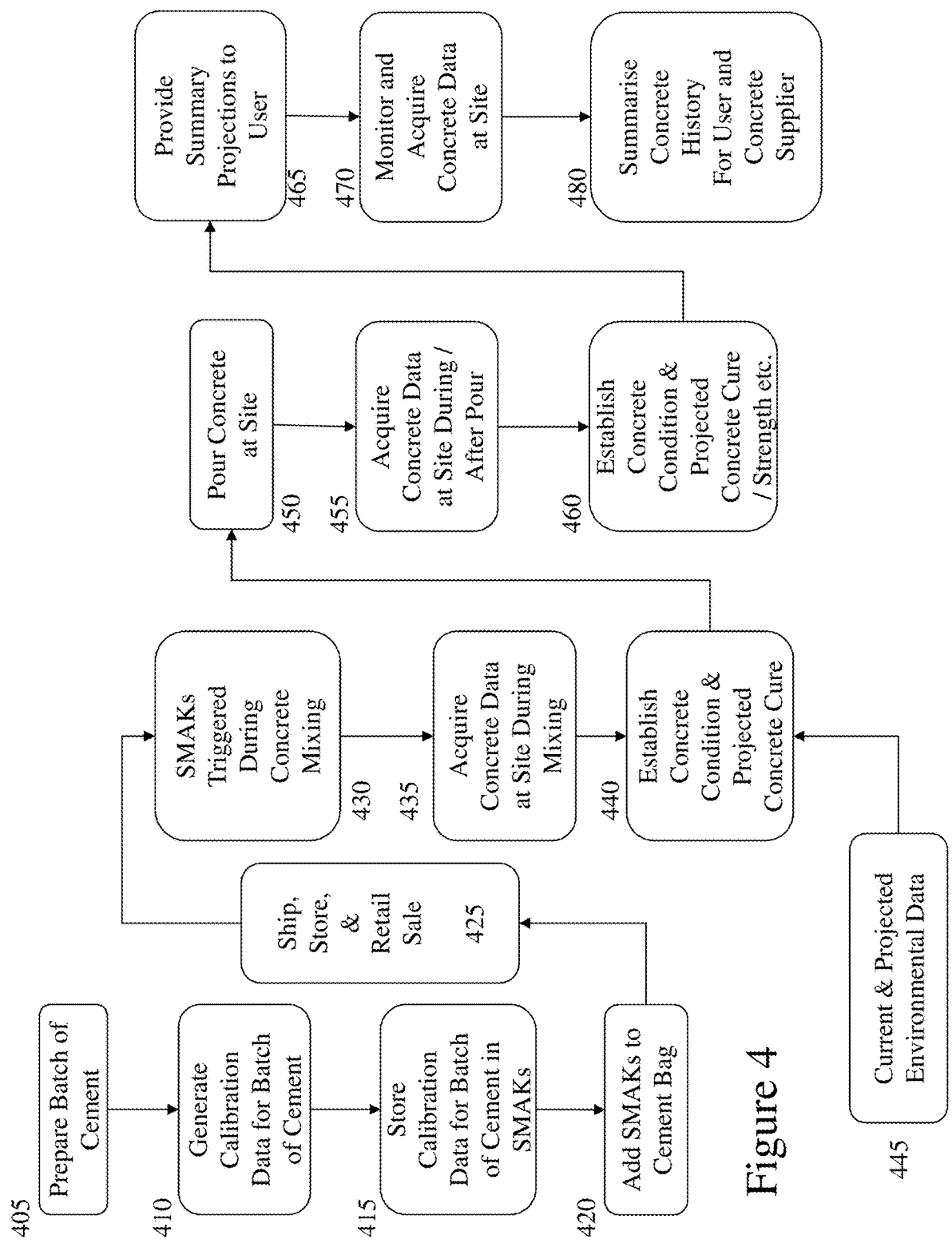
FIG. 4 depicts an exemplary process flow for an embedded sensor methodology for data logging concrete properties for concrete mixed at a worksite from "bagged" cement from initial mix through pouring, curing, and subsequently according to an embodiment of the invention.

Now referring to FIG. 4 there is depicted an exemplary flow for SMAK methodology for data logging concrete properties from initial mix through pouring, curing, and subsequently according to an embodiment of the invention wherein the SMAK is deployed in conjunction with a bag of cement (e.g. Portland cement) which is subsequently used to make a batch of concrete. Whilst the following description relates to a bag of cement it would be evident that the methodology described may be similarly employed with a pre-packaged concrete mix comprising cement, sand, and ballast to which only water is required to be added. Alternatively, it may be a mix of dry ingredients such as aggregate, an admixture, a supplementary cementitious material. Optionally, the SMAK may be part of a fiber bag filled with pre-package concrete mix designed to be laid down and absorb water through natural processes such as rain water, flood water etc. or by being watered from a spout, hose, water tanker etc. Optionally, the SMAKs may be sold discretely from the mix for the user to add when mixing the concrete, for example, within a small mixer or on the ground rather than a large commercial mixing truck.

Accordingly, the process begins with step 405 wherein a batch of cement is prepared wherein in step 410 the calibration data, for example the maturity calibration curves, is generated for that batch. Next in step 415 this calibration data is stored within a batch of sensors which will be embedded with the cement. Optionally, in an addition step which is not depicted, additional data such as date, time, location, order data, manufacturer identity, etc. may be added to the SMAKs. Once the sensors have been embedded with the data then they are mixed/embedded into the concrete for delivery. Subsequently, in step 420 the SMAK or SMAKs are added to the cement bag. This may for example, be via placement of the SMAK(s) within a container (e.g. plastic pouch), attached to the cement bag, typically internally, such that they can be subsequently retrieved and deployed. For example, a bag of cement may include 1, 2, 3, or more SMAKs with instructions that a particular number of SMAKs are added to a concrete mix made with, for example, quarter of a bag of cement, half a bag of cement or a full bag of cement, for example. At this point the bag of cement or concrete mix is stored, shipped to a retail store, stored and subsequently purchased and used.

Accordingly, the SMAKs may monitor the cement storage, shipment, storage and deployment process based upon data logging performed continuously or temporarily upon detection of an event such as movement of the bag. Alternatively, the SMAKs may be passive until activated at mixing such as closure of an electrical contact through the water employed within the mixing process, for example. Accordingly, the triggered active SMAKs in step 430 acquire data during the concrete mixing in step 435 which is processed to establish concrete condition and projected concrete cure based upon the SMAK data in step 440 which is either processed by the SMAK and communicated to a PED executing an application to accept data from the SMAKs or data is transferred to the PED and then used by an application in execution upon the PED. Wherein processing of the data is performed on a PED at the worksite then the application may extract current and projected environmental data 445 from a service, e.g. a web based weather network.

Subsequently, in step 450 the concrete is poured at the worksite and the SMAKs continue monitoring in step 455. Next the data from the sensors is retrieved either in a single retrieval event or multiple events such that in step 460 the concrete condition, projected cure, projected strength, etc. are established. Next in step 465 summary projections are provided to the PED or another PED wherein a decision on the concrete may be made as to whether it will be allowed to continue curing or whether there is a problem and remedial work/tear-down etc. are required at which the process proceeds to step 470 wherein the SMAK(s) continue to acquire data for a long as their internal battery allows or subsequently where remote powering through RFID and/or HIRES-WIPO provides power to perform a data acquisition and wireless transmission.

Figure 5:
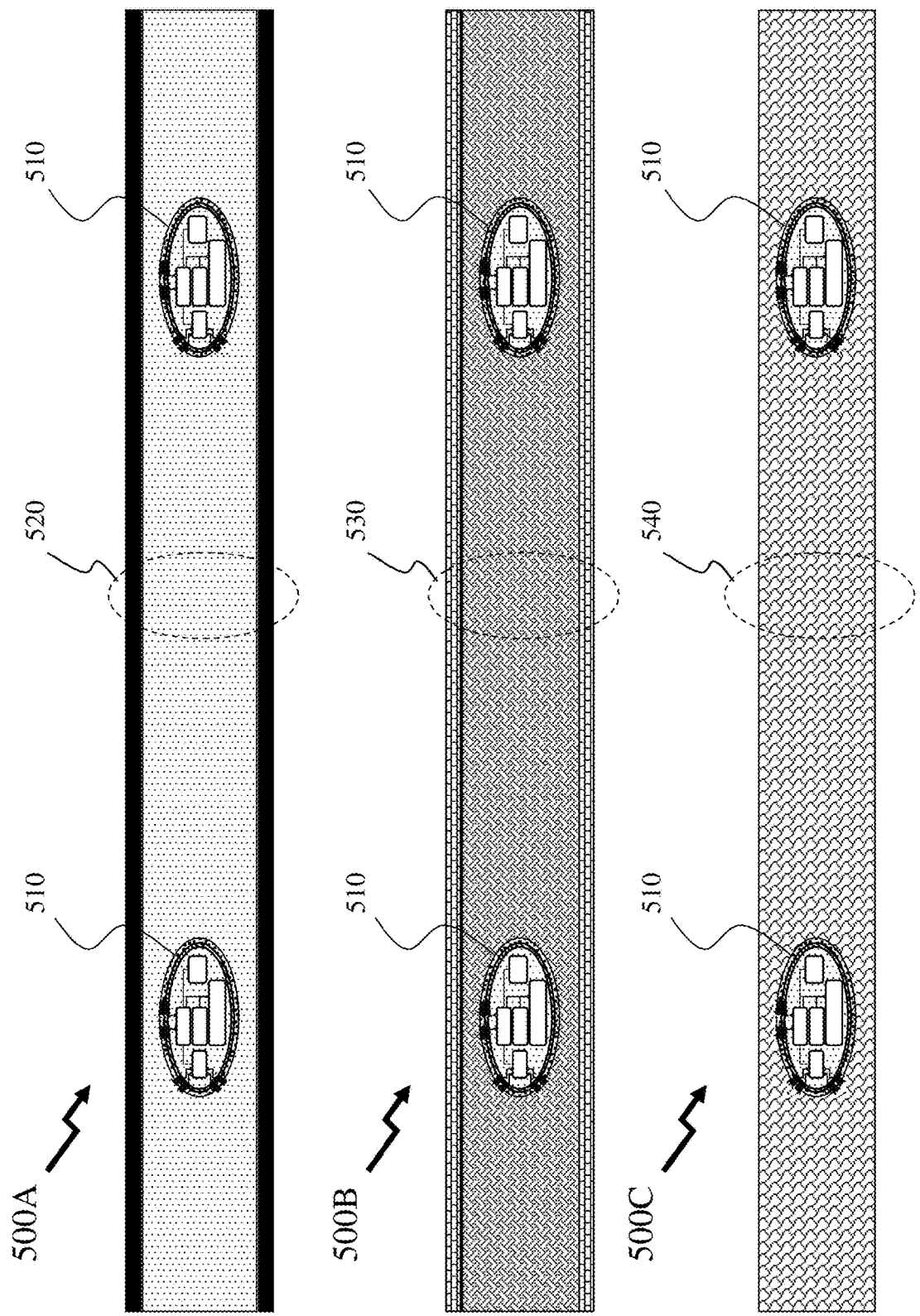
FIG. 5 depicts examples of embodied sensors employed within other manufacturing materials for logging manufacturing and/or se parameters according to embodiments of the invention.

Whilst the SMAKs have been described with respect to their use within concrete it would be apparent that variants may be employed within other materials in order to monitor, log, track, and verify aspects of their transport, delivery, and use. For example, SMAKs 510 may be employed as depicted in FIG. 5 within gypsum board 520 in first image 500A, particle board 530 in second image 500B, and a fiber board 540 (e.g. medium density fiberboard—MDF) in third image 500C. Within gypsum board 520 the SMAKs may be mixed within the gypsum slurry as it is applied or placed within the gypsum slurry just as the upper sheet is applied, for example. Similarly, within particle board 530 and fiber board 540 the SMAKs 510 may be mixed with the wood particles/fibers respectively as rolled out. Accordingly, SMAKs can provide data relating to the storage and deployment of the material they are embedded within. In such instances the parameters measured may vary with the product being manufactured. Similarly, the data stored within the SMAKs during the manufacturing of the product may be varied.

SMAKs according to embodiments of the invention may be formed from a variety of materials include, but not limited, to metals, ceramics, plastics, resins, and rubbers according to the requirements for compatibility with the concrete, lifetime, crush resistance etc. Optionally, the SMAKs may be hollow or solid with cavities for electronics/battery etc. Optionally, the SMAK may comprise a plurality of metallic elements isolated with respect to each other to form electrical connections between the electronics within the SMAK and the concrete.

It would be evident that the use of products with embedded SMAKs such as bag cement, for example, may be regulated for instances where the bag cement is employed in a structural element of a construction activity, e.g. making steps, floors, supporting beams, etc. but be optional or unnecessary in other applications, e.g. making a path. Optionally, the data acquired from one or more SMAKs with a PED executing an application communicating to and/or retrieving data from the SMAKs may push the data to one or more cloud storage locations for subsequent retrieval by one or more parties including, but not limited to, product manufacturer, retailer, contractor, and regulatory authority.

Figure 7:
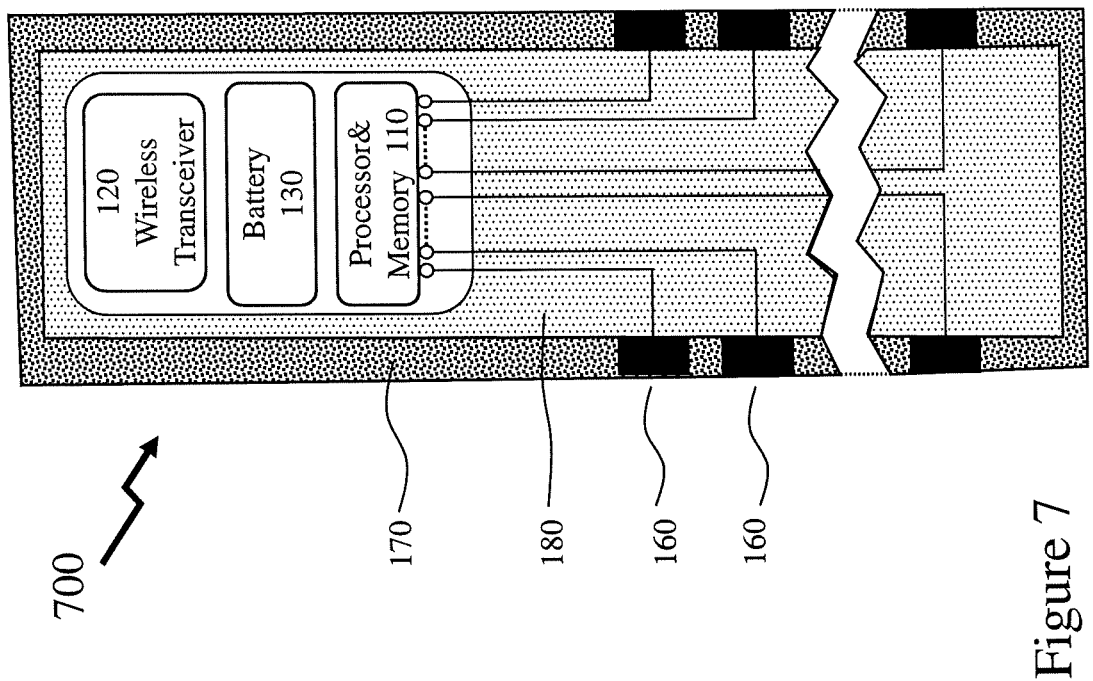
FIG. 7 depicts an embedded sensor according to an embodiment of the invention with multiple sensors distributed along the length of the sensor allowing for the measurement of gradients during concrete curing, for example.
Figure 6:
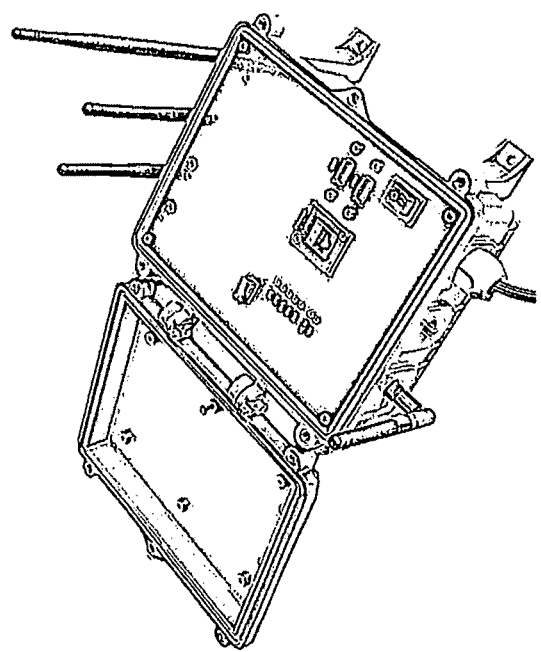
FIG. 6 depicts a ruggedized hub according to an embodiment of the invention for work site deployment and communications to embedded sensors and local wireless network for remote server access etc.

Within the embodiments of the invention presented supra in respect of FIGS. 1 to 5 and below in respect of FIGS. 6 to 8 particular emphasis has or may have been placed upon the SMAK as a discrete device communicating to a remote terminal, PDA, hub, PED, FED etc. However, it would be evident that multiple SMAKs may communicate to a single remote terminal, PDA, hub, PED, FED etc. and that the multiple SMAKs may communicate with each other and form an ad-hoc network or multiple ad-hoc networks with communication to the remote terminal, PDA, hub, PED, FED etc. undertaken via a master node within an ad-hoc comprising master é slave nodes or any nodes able to access the remote terminal, PDA, hub, PED, FED etc. Referring to FIG. 6 there is depicted a ruggedized hub according to an embodiment of the invention established by the inventors. The hub can communicate with SMAKs and other environmental and/or monitoring sensors as well as coupling to one or more local wireless networks in order to access remote storage, e.g. cloud-based storage on remote servers.

Within the embodiments of the invention presented supra in respect of FIGS. 1 to 6 and below in respect of FIGS. 7 to 8 particular emphasis has or may have been placed upon the SMAK as a discrete device with single sensor or multiple sensors operating at a single location within a formwork of poured concrete. However, referring to FIG. 7 there is depicted a SMAK according to an embodiment of the invention. As depicted the SMAK 700 comprises processor 110, wireless transceiver 120, and battery 130 together with multiple sensors 160 with a shell 170 and filler 180. With multiple sensors 160 distributed along the SMAK 700 measurements may be made of temperature gradient(s) and/or humidity gradient(s) through the user of multiple temperature sensors and/or multiple humidity sensors. The measurement of gradients is critical in concrete industry as it is important to ensure the temperature gradient is not too high, for example below 20° C. to prevent cracking. With respect to humidity it is important to measure the evaporation rate or drying/wetting rate. It would be evident that the concrete surface dries faster but a SMAK embedded within the cross section of the concrete can be very useful in monitoring the humidity changes and gradients.

It would evident that the SMAK may include a single or multiple pressure sensors allowing the depth at which the SMAK sensor is embedded within the concrete to be calculated based on the hydraulic pressure of the fresh wet concrete. This information can be used for adjusting the curing temperature or applying the floor covering when it reaches a certain humidity level.

Figure 8:
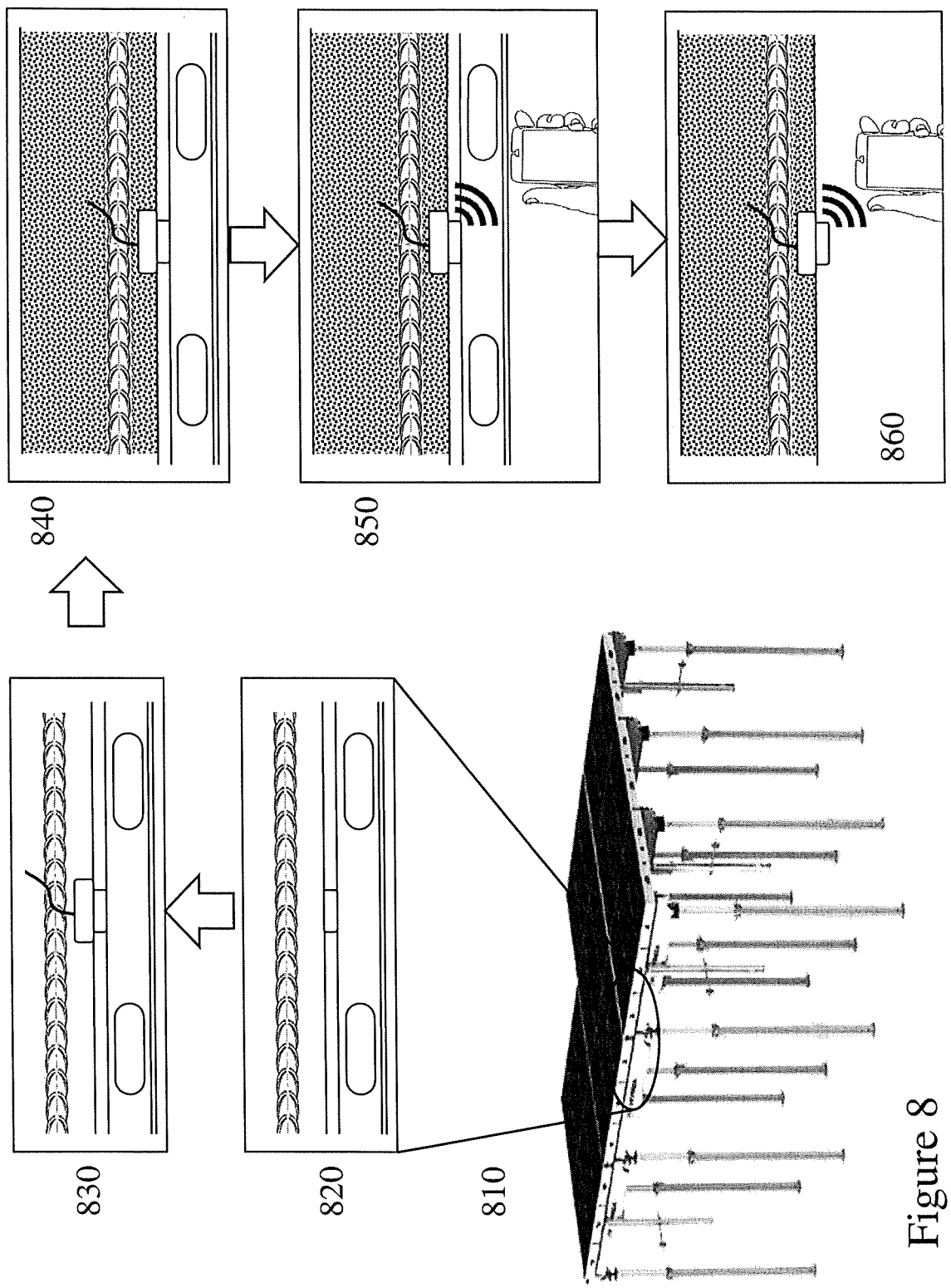
FIG. 8 depicts a schematic deployment method for embedded sensors according to embodiments of the invention in conjunction with formwork.

Now referring to FIG. 8 there is depicted an alternate methodology according to an embodiment of the invention wherein SMAK(s) are embedded in or mounted onto formwork panels. Accordingly, referring to FIG. 8 a formwork is depicted in first image 810 comprising a series of panels which in this instance are upon posts for the formation of a concrete ceiling/roof. Accordingly, as depicted in second image 820 the panel(s) have mounting points for the SMAK(s) such that as depicted in third schematic 830 the SMAK is added to the formwork which may already have rebar formed across. Subsequently, as depicted in fourth image 840 the concrete is poured onto the formwork such that the end user can monitor in fifth image 850 the concrete curing/setting. Subsequently, with the removal of the framing of the formwork the end user may continue to monitor the subsequent cure and performance of the concrete. In this manner the formwork company may sell smart panels with the relevant information in the sensor. The sensors could have multiple leads for monitoring the temperature of concrete as well as the ambient temperature for curing optimization. It can also have a LED light to go green when the strength reaches a certain level and the formwork is ready to strip or vibrate/buzz etc.

Within the embodiments of the invention presented supra in respect of FIGS. 1 to 8 particular emphasis has or may have been placed upon the storing of data relating to the material(s) being monitored within the SMAK(s). However, within an alternate embodiment of the invention the SMAK performs only measurements with or without calibration according to the design/configuration of the SMAK. The acquired sensor data is then transmitted to a local or remote host such as a remote terminal, PDA, hub, PED, FED etc. Considering, a user employing a smartphone then their smartphone has installed upon it an application associated with the material and/or a material producer depending upon the willingness of the material producer to have their calibration information within a multi-producer application or solely an application linked to them. Accordingly, a material producer, for example a concrete producer may upsell their concrete to an end user as "smart concrete." Within this embodiment of the invention the SMAKs may be within the concrete as delivered by the producer's but within other embodiments of the invention the producers may deliver the concrete without SMAKs. The end user may purchase these from the concrete producer and install them in their job site. The end user will then download or access the concrete producer's application, assign the corresponding mix name to the SMAK(s) deployed and obtain data relating to their concrete pour such as strength values and other parameters.

Figure 9:
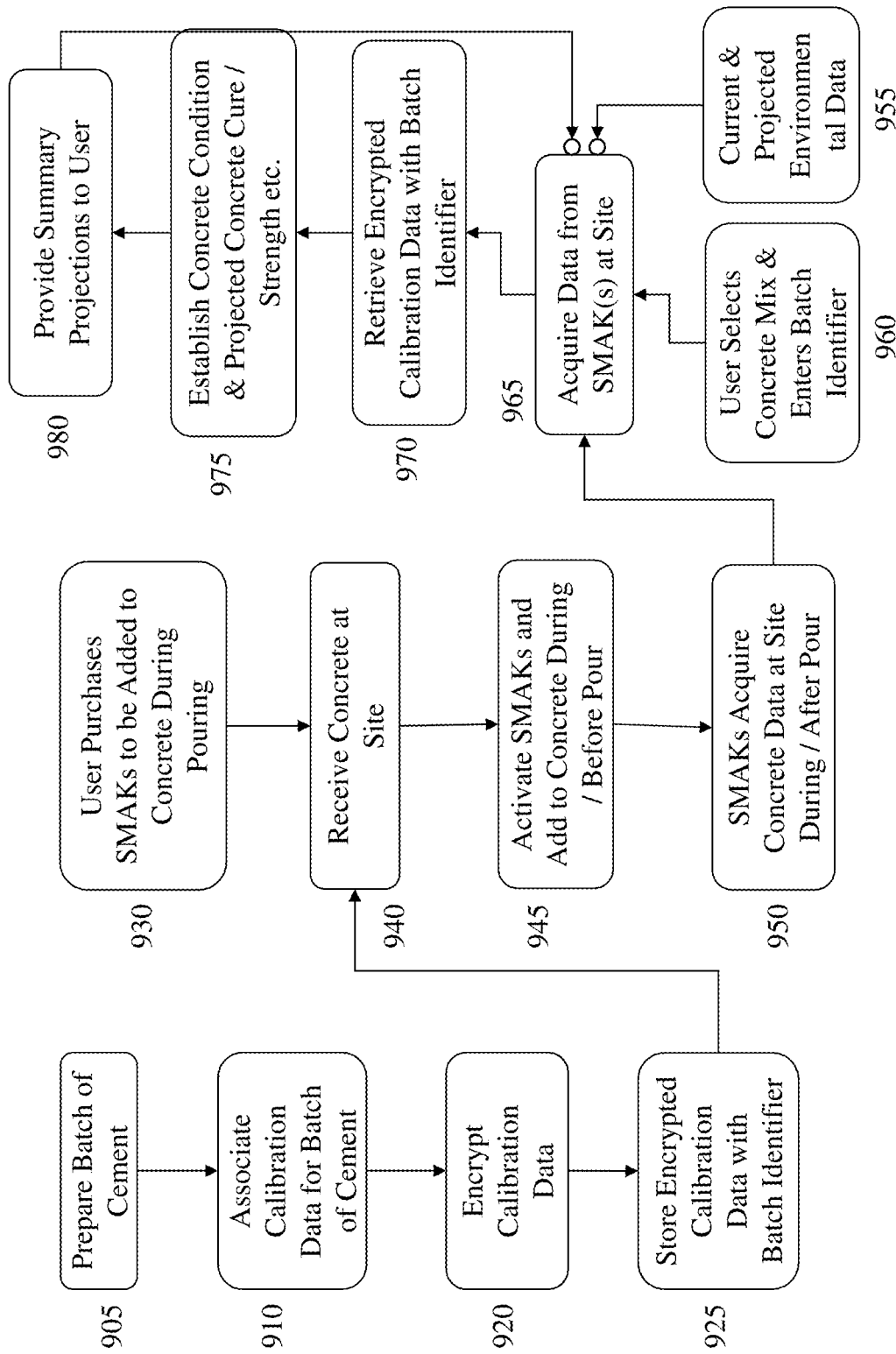
FIG. 9 depicts an exemplary process flow for an embedded sensor methodology for data logging concrete properties for concrete delivered to a worksite wherein the characteristics of the concrete are stored within a PED/cloud datafile accessible to a software application downloaded to a user's PED where the user merely selects the mix procured.

Now referring to FIG. 9 there is depicted an exemplary flow for SMAK methodology for data logging concrete properties from pouring, curing, and subsequently according to an embodiment of the invention wherein the SMAK is deployed in conjunction with poured cement. Whilst the following description relates to delivery of pre-mixed concrete it would be evident that the methodology described may be similarly employed with on-site concrete preparation a pre-packaged concrete mix comprising cement, sand, and ballast to which only water is required to be added. Accordingly, the process begins with step 905 wherein a batch of cement is prepared wherein in step 910 the calibration data, for example the maturity calibration curves, are associated with that batch. Next in step 920 this calibration data is encrypted and then in step 925 this encrypted calibration data is stored within cloud storage together with the batch identifier for subsequent retrieval and use by a software application in execution upon a PED and/or FED. The mixed concrete is delivered to the worksite in step 940. At a preceding point in time the user purchases one or more SMAKs which they intend to add to the concrete pour(s) at the worksite. Accordingly, in step 945 the SMAKs are activated (if necessary) and added to the concrete during the pour or as discussed supra in respect of FIG. 8 these SMAKs may pre-located within the formwork of the worksite prior to the concrete pour.

Accordingly, in step 950 the SMAK(s) acquire data from activation onwards which is subsequently acquired in step 965 from the SMAK(s) through a device such as PED executing a SMAK software application (SSA) which can communicate with the SMAK(s) directly, through a hub such as depicted in FIG. 6, or accesses a hub which consolidates data from a plurality of hub(s). The SSA in step 965 also accumulates current and/or projected environmental data from local sensors, PED sensors, online resources, etc. which was acquired in step 955 and the concrete mix/batch information in step 960. The SSA then retrieves the encrypted calibration data of the concrete mix wherein the decryption key is unique to the batch identifier and provided to the user with the batch delivery. Accordingly, using the retrieved calibration data in combination with the acquired SMAK(s) data the SSA establishes in step 975 the concrete condition as well as projected cure/strength information are established and then provided to the user in step 980. These process steps 965 to 980 may be repeated periodically by the user.

Optionally, the SSA may simply push data to a remote cloud server for processing in combination with the decrypted concrete calibration data etc. such that whilst the results are provided back to the user's PED/SSA they are also archived upon the remote server. Optionally, the SSA and/or remote application may store raw SMAK data as well as the processed data from the SMAK(s). Optionally, a tagged SMAK may be deployed with the concrete which has been added by the concrete producer so that the specific mix is identified from the tagged SMAK rather than mix selected by the user from a drop-down menu.

Within embodiments of the invention the SSA may be generic such that any manufacturer/provider of concrete may exploit the SSA/SMAKs provided that their calibration data is formatted according to the SSA file format. A manufacturer may elect to store their calibration data within the SSA/remote database in encrypted or non-encrypted form. Within other embodiments of the invention the SSA may be specific to a manufacturer/producer wherein the SSA may upon selection of a mix of that manufacturer/producer extract data from specific web locations exploiting coded HTML addresses against that specific mixture.

Within other embodiments of the invention this concept may be extended to bagged concrete, for example. Instead of putting the sensor in the bag, the sensor will be offered/purchased separately by the end user. The end user then gets the mix assigned to the sensor through scanning, for example, a QR code, bar code, or entering a product identifier to the mobile application or web based application depending on what they use. Within these embodiments of the invention the concrete producers do not release proprietary mix calibration information. Rather this is stored upon a remote server executing an application to which the web based application and/or mobile application communicate. Alternatively, the information may be downloaded to a PED executing a mobile application in an encrypted form and a subscription/registration etc. may be required in order for the user's PED to acquire the decryption key.

Within the embodiments of the invention presented supra in respect of FIGS. 1 to 9 particular emphasis has or may have been placed upon electrical measurements as the basis of a sensor with respect to determining a property of the medium within which the sensor is disposed. However, it would be evident to one of skill in the art that in addition to DC resistance(s), DC potential(s), AC resistance(s), AC potential(s), conductivity etc. that sensors may be configured with a SMAK or within different SMAKs for a range of parameters including, but not limited to, temperature, pressure, light, acceleration, humidity, vibration, pH, and chloride content. More advanced SMAK(s) may provide dedicated hardware, functionality, and software to enable more advanced techniques such as nuclear magnetic resonance, electrochemical, X-ray diffraction, optical spectrometry, thermogravimetric analysis, a half cell, etc. as well as corrosion resistance etc.

Within the embodiments of the invention presented supra in respect of FIGS. 1 to 9 particular emphasis has or may have been placed upon inclusion of a battery within the SMAK(s). Such a battery may be charged and connected permanently to the internal circuitry of the SMAK or connected based upon an event/trigger. In some embodiments of the invention the SMAK may be in a low power sleep mode until awoken by wireless command. Alternatively, detection of conduction between pins via the wet concrete, vibration, impact, pressure etc. may form events/triggers in isolation or combination. In other instances, the SMAK is only charged at the time it is going to be deployed such as through a wireless charging interface. Within other embodiments of the invention electrical power may be generated by the SMAK such as through piezoelectric charging, electrochemical charging from electrodes in the alkaline pore solution in concrete etc. Piezoelectric charging may be via vibration, strain, compression, etc.

Within the embodiments of the invention presented supra in respect of FIGS. 1 to 8 particular emphasis has or may have been placed upon the storing of parameters relating to cement and/or concrete upon a SMAK. However, it would be evident that in other embodiments of the invention the parameters may relate to mortar or an admixture for addition to concrete. Further, in other embodiments of the invention the parameters may relate to one or more components of the material being monitored, such as a glue within chipboard/fiberboard manufacture (e.g. MDF), a resin and é or fiber within fiber reinforced composites/fiberglass etc.

Optionally, the SMAK may be associated with a product, e.g. a bag of cement without any data for the properties etc. being stored within it. Accordingly, the requisite data may be attached to the product at a subsequent point in time through the use of a barcode, RFID tag, tag etc. and subsequently read by a PED for entry into an application in execution upon the PED wherein the SMAK is subsequently "programmed" based upon data being communicated to it from the PED. Optionally, the SMAK may be a smart tag attached to the packaging which is interrogated during the storage, shipment, retail stages of the product life cycle such that the SMAK is updated at each stage as a result of the interrogation with data relating to that interrogation etc.

Within another embodiment of the invention a SMAK may include one or more vibratory elements such that the SMAK may vibrate and adjust its depth within the freshly poured concrete based upon pressure measurements to determine when the SMAK is at the right depth. The SMAK may move towards the concrete surface or move to the bottom based upon depending upon the density of SMAK. In other embodiments of the invention the SMAK may position itself such that wireless reception is achieved.

B. Advanced Maturity Method

Early, rapid and accurate in-situ estimation of the compressive strength of concrete is one of the major challenges for the concrete industry. An accurate and reasonable in-situ estimation of the compressive strength provides the opportunity to optimize the concrete mix design as well as optimizing the formwork removal time. The optimization of mix design affects the consumption of raw materials (e.g. cement and aggregates) and alternative materials (e.g. natural pozzolans and supplementary cementitious materials like fly-ash and silica-fume). Considering the high volume global consumption of concrete, this could, in turn, effectively optimize the consumption of resources and reduce a great extent of $CO_2$ and toxic materials (emitted during the cement production) into the atmosphere.

The maturity method is a convenient approach to predict the early age strength gain of concrete, using the principle that the concrete strength is directly related to the hydration temperature history of cementitious paste. The maturity concept for estimating the strength gain of concrete is described in American Society for Testing and Materials (ASTM) standard C1074, "Standard Practice for Estimating Concrete Strength by the Maturity Method". This method can potentially address many immediate challenges facing the concrete industry such as predicting appropriate time for formwork stripping and post-tensioning, especially at low temperatures while the strength development of concrete is hindered; and optimizing concrete mix design and concrete curing conditions (e.g. concrete heating at low temperatures or surface protection in hot-dry weathers). Lack of an accurate estimation of strength at early ages of construction is twofold: contractors either wait too long for next action (e.g. stripping formwork) which is costly due to delays in completing the project, or they act prematurely which could cause the concrete structure to crack—that would lead to future durability and performance issues—or even structural collapse.

In most construction sites, field-cured concrete samples are tested to strength at various ages during the first week since concrete is poured, in order to make a decision on formwork removal. For example, ASTM C873 offers a test method for cast-in-place cylindrical specimens. These specimens can be removed later for measuring the compressive strength of concrete in the lab. Usually, if the concrete reaches 75% of its designed strength, the structural engineers allow for the striping of forms. The problem, however, is that only one specimen is crushed for strength estimation. This is not necessarily accurate. This method is limited to use in horizontal and thick concrete elements like slabs. In addition, the construction crew is usually on the job site while they are waiting to hear about the compressive strength result from the laboratory. This adds to the cost of construction and its uncertainty decreases the efficiency of the construction. Although alternative methods such as concrete maturity exist, there is a traditional resistance to utilizing them for most concrete projects. Such approaches to compressive strength evaluation may cause concrete contractors to make conservative decisions, face more complicated technical problem (e.g. delay in formwork stripping, and unnecessary long-term curing and surface protection), and spend more financial resources.

B.1: Maturity Method

As a non-destructive testing, the maturity method may be a reasonable candidate to fill this gap. In comparison to most on-site non-destructive technologies (e.g. Schmidt Hammer or Ultrasonic Pulse Velocity), the privilege that the maturity method stands on is that, the procedure for estimating the compressive strength would be objective and qualitative once the maturity curve is developed and adopted.

The maturity method is a relatively simple approach for estimating the in-place compressive strength of concrete, specifically at early ages less than 14 days. Once the maturity curve is developed in the laboratory for a specific project, it can be used for on-site estimation of compressive strength of concrete in real-time. The maturity method is governed by the fundamental assumption that a given concrete mix design poured during course of a specific project has the same compressive strength when it has the same "maturity index". This means that a given concrete mix design, for example, may reach the same compressive strength after 7 days of curing at 10° C. when it is cured at 25° C. for 3 days.

The maturity method based on the ASTM C1074 is the most commonly used method to estimate the in-situ strength of concrete today within the industry. ASTM C1074 provides two maturity functions: 1) Nurse-Saul function; and 2) Arrhenius function. Based on the Nurse-Saul method, there is a linear relationship between the maturity and the temperature in real time. The underlying assumption is that the strength development in concrete is a linear function of hydration temperature. Equation (1) shows the relationship between maturity and hydration temperature history where M(t) is the maturity index at time t, $T_{AVG}$ is the average temperature during the time interval $\Delta t$, and $T_0$ is a datum temperature.

$$M(t)=\Sigma[(T_{AVG}-T_0)\cdot \Delta t] \quad (1)$$

ASTM C1074 provides a standard procedure to find the datum temperature for a specific mix design. However, most of previous studies suggest a practical estimation of the datum temperature between $-10° C.\leq T_0\leq 0° C$. Indeed, this is the temperature at which the hydration of cementitious paste stops; hence the strength development of concrete ceases. The inventors have established that this datum temperature lies between $-5° C.\leq T_0\leq 0° C$. dependent on the concrete mix design.

The second approach is the Arrhenius function that assumes there is an exponential relationship between the compressive strength and hydration temperature. The maturity index is defined in form of an equivalent age at a reference temperature. It means the actual age should be normalized to the reference temperature in order to estimate the compressive strength. This function needs a value of activation energy that can be determined as the procedure detailed in ASTM C1074. Despite the fact that the Arrhenius function is scientifically more accurate, the Nurse-Saul function is more commonly used by concrete industry for the following reasons:

accuracy of the Nurse-Saul function is adequate for most field applications;

the Nurse-Saul function is relatively simpler compared with the Arrhenius function.

There is another method proposed by Papadakis and Bresson for the calculation of Maturity index called weighted maturity. In this method the weighted maturity is expressed by Equation (2) where M(t) is the weighted maturity (° C.·h), $t_K$ is the hardening time of concrete corresponding to $(T_i-T_j)/2$, $T_K$ the hardening temperature interval $(T_i-T_j)$ in ° C., C is an experimental coefficient which depends on the cement type and $n_K$ is the temperature-dependent parameter for $T_K$. This maturity method is adopted by Dutch standard NEN 5970, entitled 5970 "Determination of Strength of Fresh Concrete with the Method of Weighted Maturity", and is currently being used in some European countries, including the Netherlands.

$$M(t)=\Sigma[t_K T_K C^{n_K}] \quad (2)$$

ASTM C1074 provides a step-by-step guide for developing the maturity curve, and for estimating the compressive strength. These steps include the following as the maturity-strength curve represents the relationship between maturity index and compressive strength for a specific concrete mix design, adopted in the laboratory. To do so, adequate concrete cylindrical specimens should be casted, and then stored in the semi-adiabatic condition for curing. Certain number of concrete cylinders (i.e., at least two concrete specimens) should be equipped by embedded temperature sensors for recording the hydration temperature history. The compressive strength of concrete is measured at ages of 1, 3, 7, 14 and 28 days. This being depicted schematically in FIG. 10.

The maturity index is calculated at strength testing times using Equation (1) and then the best curve will be fitted for the strength data versus maturity index data to obtain the maturity-strength curve as given by Equation (3) where M is the Maturity index, S is the in-situ compressive strength of concrete, and a and b are the experimental coefficients.

$$S=a+b\cdot \log(M) \quad (3)$$

Figures 10, 11:
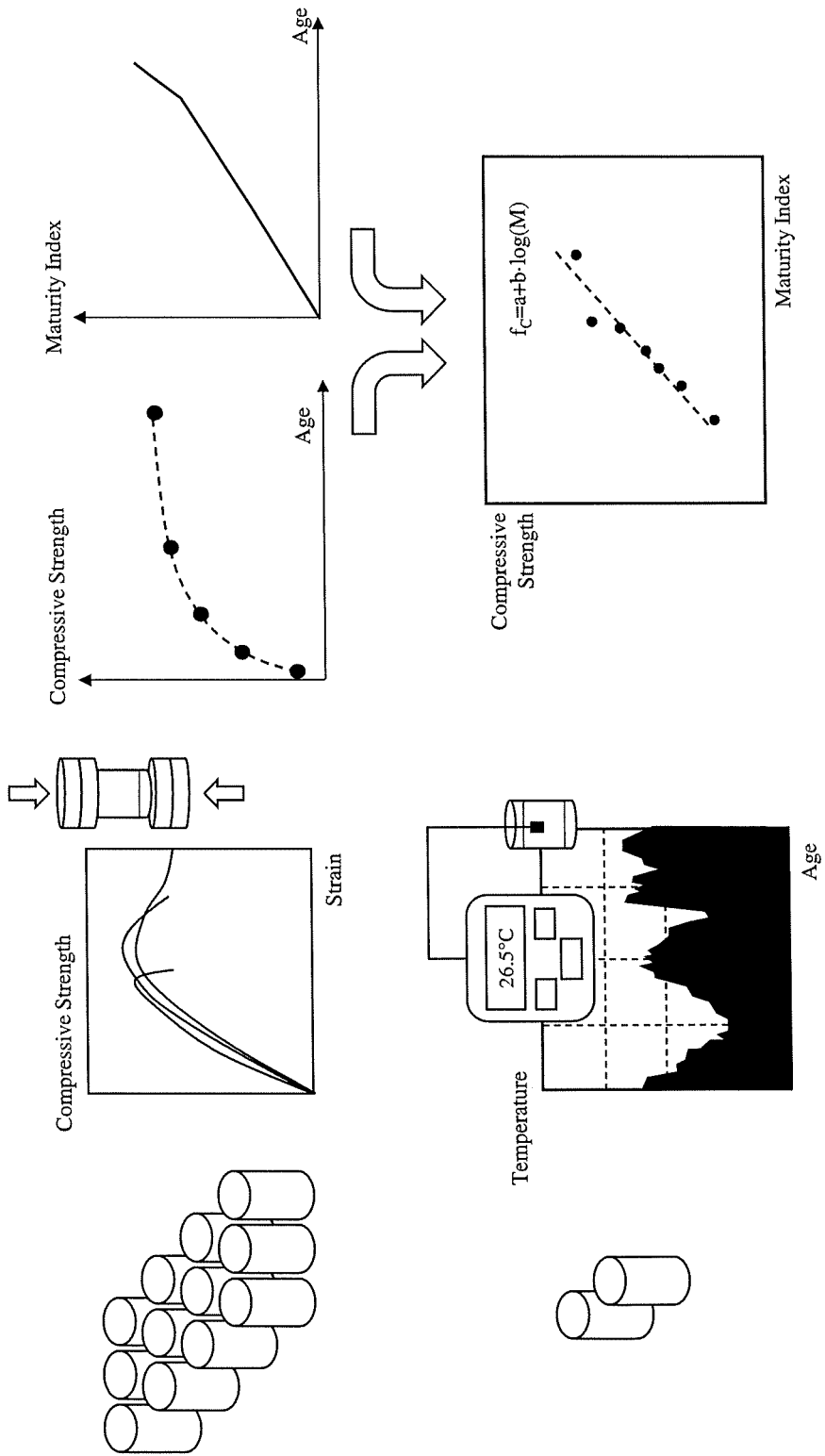
FIG. 10 depicts the prior art process of establishing maturity for concrete under ASTM C1074.
FIG. 11 depicts the periodic monitoring under ASTM C1074 wherein the maturity index is calculated at different strength testing times and the best curve fitted for the strength data versus maturity index data to obtain the maturity curve.

This is depicted schematically in FIG. 11. It should be noted that it is important to test the concrete mix design that will be the same as that used in the construction project. Any deviations from the original mix design (such as water to cement ratio, cement content, etc.) will reduce the accuracy of the maturity method to estimate the compressive strength.

Once the maturity-strength curve is developed, it can be used to estimate the in-place concrete strength using the hydration temperature history. To do so, the temperature history of the concrete elements should be recorded after pouring using embedded sensors at the locations that are generally critical in term of exposure conditions, curing and structural requirement. Routine quality control tests should be performed to ensure the accuracy of the maturity-strength curve. These controls minimize any error in the estimation of in-place strength due to inherent limitations of the maturity method.

Some of important limitations of this method are listed as follows:

In-place concrete is not representative of the concrete used to develop the calibration in the lab. This can be because of changes in materials, water to cement ration, air content, batching method, etc.;

In-place concrete is not properly placed, consolidated, cured, etc.;

Very high early-age temperatures can lead to inaccurate estimation of strength at later ages;

Using a datum temperature (for the Nurse-Saul function) that is not representative of the concrete mixture can result in incorrect estimation of strength.

Figure 12:
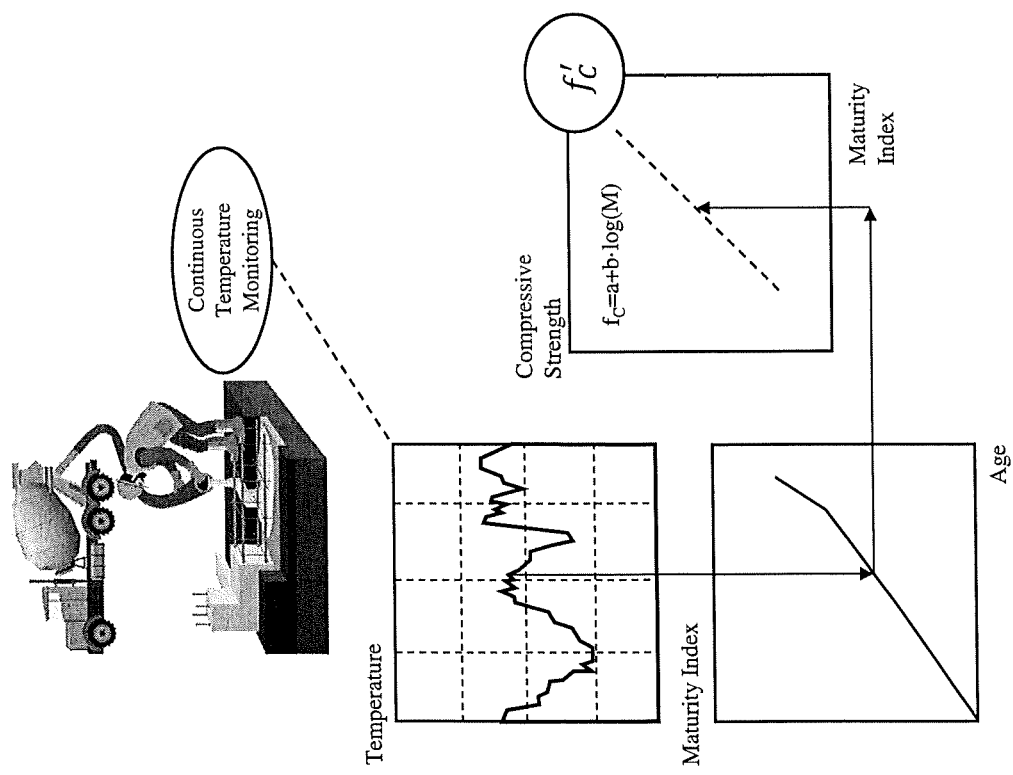
FIG. 12 schematically depicts how exploiting prior art test instruments employing ASTM C1074 estimate concrete strength from the maturity curve generated by the process depicted in FIG. 12.

Within the prior art several maturity devices have been established that can measure the hydration temperature of concrete in real time. Most of these devices can calculate the maturity index and predict the compressive strength if the maturity-strength curve, datum temperature and any required information are developed. Most of these devices include a temperature sensor embedded into the concrete elements that is plugged in the data logger via an electrical cable. Alternatively, a simple thermocouple could be embedded in concrete for temperature monitoring using a connected data logger. The data should then be extracted and used to calculate the maturity index and use it to estimate the concrete strength from the maturity curve. This is depicted schematically in FIG. 12.

B.2 Advanced Maturity Concept

Except for specific and critical projects, the concrete industry shows interest in the commonly used compressive strength test. This is mainly due to the upfront cost of concrete mixture calibration for maturity curves, and lack of expertise for the installation of concrete temperature sensors, data collection and analysis. However, the inventors have established an advanced calibration technique to develop Maturity-Strength curves without the need to test the compressive strength of concrete in the laboratory at all five ages (i.e., breaking 15 concrete specimens at ages of 1, 3, 7, 14 and 28 days). Within the embodiment of the invention according to the method established by the inventor's data from the electrical resistivity and concrete temperature is combined to derive the coefficients in the concrete maturity-strength relationship (i.e., a and b) without the need to conduct extensive compressive strength measurements.

An example of such combined calculations is described as follows. In this example, only one compressive strength test will be required at a standard age such as 7 or 28 days for example. The details of the technique are described below. The data established by the inventors shows that the compressive strength of concrete is the logarithmic function of the electrical resistivity of concrete in the saturated concrete condition as given by Equation (4) where ρ is the electrical resistivity of concrete in saturated condition, S is the in-situ compressive strength of concrete, and c and d are the experimental coefficients, which are mix dependent.

$$S = c + d \cdot \log(\rho) \tag{4}$$

From Equations (3) and (4) the inventors derive the relationship between ρ and M as given by Equation (5). Then by curve fitting of the experimental data, i.e. log(M) and log(ρ) in Equation (5) the relationships given by Equations (6) and (7) are derived where $X_1$ and $X_2$ are the intercept and slope coefficients obtained from the regression analysis (curve fitting).

$$\log(\rho) = \frac{(a-c)}{d} + \frac{b}{d} \cdot \log(M) \tag{5}$$

$$\frac{(a-c)}{d} = X_1 \tag{6}$$

$$\frac{b}{d} = X_2 \tag{7}$$

Figure 13:
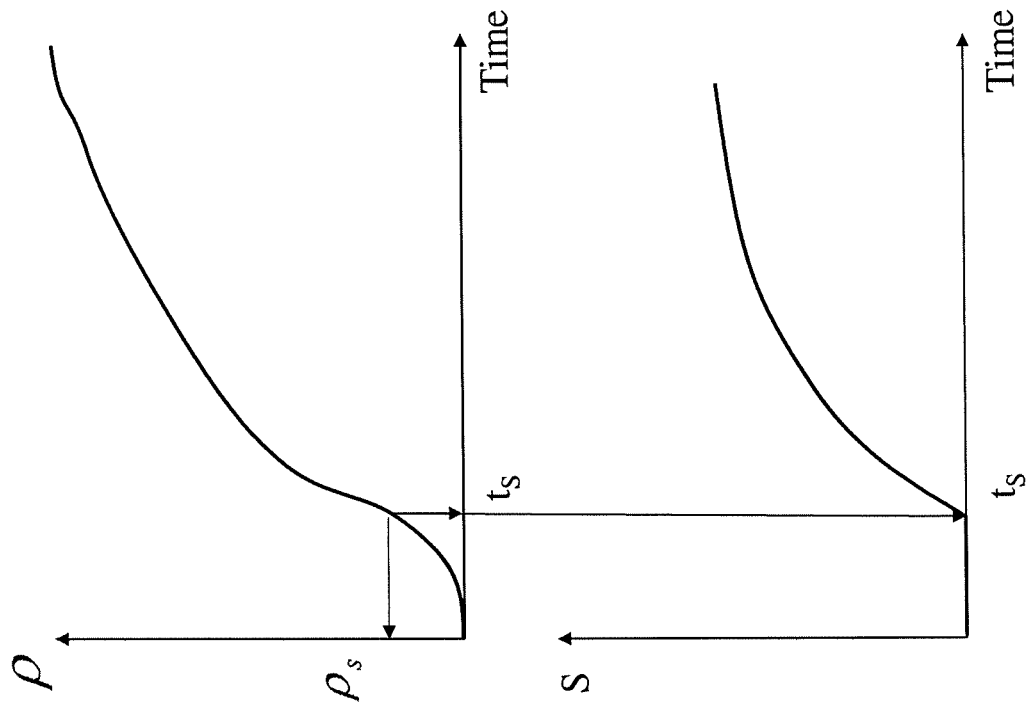
FIG. 13 depicts the electrical resistivity versus time curve of concrete whereby the resistivity value at which the concrete starts gaining strength can be identified from the inflection point in the curve.

From the electrical resistivity-time curve, one can identify the resistivity value at which the concrete starts gaining the strength (i.e., the time at which "final setting" occurs in fresh concrete) which corresponds to the time when electrical resistivity increases rapidly (e.g. the inflection point on the curve shown) as depicted in FIG. 13. Therefore, by substituting in Equation (4) we obtain the relationship in Equation (8) where $\rho_S$ is the electrical resistivity of concrete at the time of strength gain initiation point (i.e. strength is zero at this point). Knowing the strength of concrete at any age such as 7 days or 28 days ($S_t$), we can also derive the relationship of Equation (9) from Equation (4) where $S_t$ is the compressive strength of concrete at time t and $\rho_t$ is the electrical resistivity of concrete at time t. By solving Equations (8) and (9) the unknown variables c and d are obtained. Substituting the values of these two variables into Equations (6) and (7) then the maturity coefficients a and b are determined which can then be used in Equation (3) for the strength prediction using the maturity concept.

$$\frac{c}{d} = -\log(\rho_S) \tag{8}$$

$$S_t = c + d \cdot \log(\rho_t) \tag{9}$$

C. Electrical Resistivity Determination in Concrete

Within embodiments of the invention described supra and depicted in respect of FIGS. 1 to 12 the "SMArt rocKs" (SMAKs) and the Advanced Maturity Method the electrical resistivity is measured as part of the measurements. It is noted that there is a temperature dependence of this measurement and that there is an associated activation energy. However, the electrical resistivity measured is also impacted by the presence of humidity and the water content of the concrete. If we were to consider calculating concrete resistivity then we would need to consider the water-cement (w/c) ratio, the temperature, relative humidity, hydration time and the cover thickness of concrete.

For a given hydration time and w/c ratio the concrete pore saturation with relative humidity may be established from adsorption isotherms or alternatively estimated from measurements made by SMAKs deployed within the concrete. Considering the w/c ratio and the degree of saturation of the concrete then a correction factor may be established to the measured electrical resistivity made with the SMAKs deployed within the concrete. For example, scaling factors for measured electrical resistivity may be scaled based upon the variation of resistivity with saturation ($S_r$) and w/c ratio according to Equations (10) and (11) respectively below for different saturation ranges and iv/c ratios wherein the coefficients are themselves functions of the saturation, i.e. $A_X = A_X(S_r)$ and $B_Y = B_Y(S_r)$.

$$\rho = +A_1(w/c)^3 + A_2(w/c)^2 + A_3(w/c) + A_4 \quad 0.4 \leq (w/c) \leq 0.48 \tag{10}$$

$$\rho = +B_1(w/c)^2 + B_2(w/c) + B_3 \quad 0.48 \leq (w/c) \leq 0.7 \tag{11}$$

It would be evident that based upon these functions or other functional descriptions for resistivity versus one or more parameters such as saturation, relative humidity, w/c, etc. that scaling factors may be established and stored within the SMAK or an application accessing the SMAK data to provide a correction of the electrical resistivity before, during, or after any other scaling applied, such as for the temperature dependent activation of electrical resistivity for example. Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system further may include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alphanumeric input unit such as a keyboard, a pointing control device such as a mouse, and so forth.

The memory includes machine-readable code segments (e.g. software or software code) including instructions for performing, when executed by the processing system, one or more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method comprising:
providing a self-contained sensor device for determining a first characteristic of a mixture of a first material within which the self-contained sensor device is to be disposed within comprising a microprocessor, a battery, a memory in communication with the microprocessor, and one or more sensors in communication with the microprocessor;

storing calibration data within the memory of the self-contained sensor device relating to properties of the first material within which the self-contained sensor device is to be disposed; wherein the microprocessor of the self-contained sensor device is configured to automatically execute a process comprising:

performing a plurality of measurements upon the mixture of the first material with a subset of the one or more sensors within the self-contained sensor at a plurality of points in time; and calculating based upon at least the plurality of measurements obtained by the self-contained sensor device and a first subset of the calibration data a first characteristic of the mixture of the first material; wherein the plurality of measurements are electrical resistivity ($\rho$) measurements of the mixture of the first material;

the first characteristic of the mixture of the first material is its in-situ compressive strength (S); and the in-situ compressive strength (S) of the mixture of the first material is established in dependence upon substituting the electrical resistivity ($\rho$) of the mixture of the first material into a predetermined formula with mix dependent coefficients;

the self-contained sensor device is initially within a initial low power sleep mode and transitions to a second mode performing measurements upon determining at least one of:

that an externally applied pressure to the self-contained sensor device established by a pressure sensor forming part of the self-contained sensor device has exceeded a predetermined threshold; and that an electrical impedance measurement established by the self-contained sensor device in dependence upon an electrical sensor of the plurality of sensors indicate a transition from a low conductivity material surrounding a predetermined portion of the self-contained sensor device to a high conductivity material surrounding the predetermined portion of the self-contained sensor device.

2. The method according to claim 1, wherein
the predetermined formula is $S = c + d \cdot \log(\rho)$ where c and d are the mix dependent coefficients.

3. The method according to claim 1, wherein
the mix dependent coefficients c and d are established by:
monitoring the electrical resistivity ($\rho$) of the mixture of the first material versus time;
determining the electrical resistivity ($\rho_s$) of the mixture of the first material at which the concrete starts gaining strength (S=0);
determining the electrical resistivity ($\rho_T$) and strength ($S_T$) of the mixture of the first material at a time (T) after the point where the mixture of the first material starts gaining strength; and
solving for c and d with the following equations:

$$c/d = \log(\rho_s)$$

; and $$S_T = c + d \cdot \log(\rho_T).$$

4. The method according to claim 1, further comprising determining with the microprocessor an inflection point in the measured electrical resistivity ($\rho$) of the mixture of the first material versus time; wherein
the inflection point denotes a point in time that the mixture of the first material starts gaining strength.

5. The method according to claim 1, further comprising shipping the self-contained sensor device as part of a shipment to a destination; and
the shipment comprises one or more self-contained sensor devices and one of:
a package of a second material used to form the mixture of the first material at the destination by the addition of water, wherein the second material is selected from the group comprising cement, mortar, an admixture for concrete, an aggregate, a slurry or paste employed in forming the first material which is a non-cementitious construction material;
a package of a second material for addition to the first material as it is mixed, wherein the second material is selected from the group comprising cement, mortar, an admixture for concrete, an aggregate, a slurry or paste employed in forming the first material which is a cementitious construction material, and a non-cementitious product employed in infrastructure construction; and
a package established in response to an order for a second material which is one or more of a cement, a mortar, an admixture for concrete, an aggregate, a slurry or a paste employed in forming a cementitious construction material, and a non-cementitious product employed in infrastructure construction.

6. The method according to claim 1, further comprising shipping the self-contained sensor device disposed either within a bag or as part of the bag; wherein
the bag is filled with the mixture of the first material which is one of a cement, a mortar mix and a concrete mix; and
the bag is designed to be laid down and absorb water through at least one of a natural process and being watered.

7. The method according to claim 1, further comprising applying one or more scaling factors to the measured electrical resistivity of the first mixture; wherein
a scaling factor of the one or more scaling factors is a variation of electrical resistivity of the first mixture with water-to-cement ratio.

8. A method comprising:
providing a first predetermined portion of a construction material comprising a first predetermined portion of a first material; and
providing a second predetermined portion of the construction material comprising at least one self-contained sensor device of a plurality of self-contained sensor devices and a second material comprising a second predetermined portion of the first material; wherein
the first predetermined portion of the construction material and the second predetermined portion of the construction material are intended to be shipped to a predetermined location for deployment as part of a construction project;
each self-contained sensor device comprises at least a microprocessor, a battery, a memory in communication with the microprocessor, and one or more sensors of a plurality of sensors in communication with the microprocessor;

the memory of each self-contained sensor device stores calibration data relating to properties of a first material within which the self-contained sensor device is to be disposed;

the microprocessor within each self-contained sensor device is configured to automatically execute a process comprising:

performing a plurality of measurements upon the mixture of the first material with a subset of the one or more sensors within the self-contained sensor at a plurality of points in time; and determining based upon at least the plurality of measurements obtained by the self-contained sensor device and a first subset of the calibration data a first characteristic of the mixture of the first material, wherein the plurality of measurements are electrical resistivity ($\rho$) measurements of the mixture of the first material;

the first characteristic of the mixture of the first material is its in-situ compressive strength (S); and the in-situ compressive strength (S) of the mixture of the first material is established in dependence upon substituting the electrical resistivity ($\rho$) of the mixture of the first material into a predetermined formula with mix dependent coefficients; and the microprocessor within each self-contained sensor device is further configured to:

activate the self-contained sensor device from an initial low power sleep mode to a second mode performing measurements; wherein activation of the self-contained sensor device is established upon determining with the microprocessor that at least one of:

that an externally applied pressure to the self-contained sensor device established by a pressure sensor forming part of the plurality of sensors has exceeded a predetermined threshold; and that an electrical impedance measurement established by the self-contained sensor device in dependence upon an electrical sensor of the plurality of sensors indicate a transition from a low conductivity material surrounding a predetermined portion of the self-contained sensor device to a high conductivity material surrounding the predetermined portion of the self-contained sensor device.

9. The method according to claim 8, wherein the predetermined formula is $S=c+d\cdot\log(\rho)$ where c and d are the mix dependent coefficients.

10. The method according to claim 8, wherein the predetermined formula is $S=c+d\cdot\log(\rho)$ where c and d are the mix dependent coefficients; and the experimental coefficients c and d were established by performing a process comprising:

monitoring the electrical resistivity ($\rho$) of the mixture of the first material versus time;

determining the electrical resistivity ($\rho_s$) of the mixture of the first material at which the concrete starts gaining strength (S=0);

determining the electrical resistivity ($\rho_T$) and strength ($S_T$) of the mixture of the first material at a time (T) after the point where the mixture of the first material starts gaining strength; and solving for c and d with the following equations:

$$c/d=\log(\rho_s)$$

; and $$S_T=c+d\cdot\log(\rho_T).$$

11. The method according to claim 8, wherein determining with the microprocessor an inflection point in the measured electrical resistivity ($\rho$) of the mixture of the first material versus time; wherein the inflection point denotes a point in time that the mixture of the first material starts gaining strength.

12. The method according to claim 8, wherein providing the second predetermined portion of the construction material comprises one of:

providing the at least one self-contained sensor device of the plurality of self-contained sensor devices within a package of the second material for addition to the first predetermined portion of the construction material at the destination, wherein the second material is selected from the group comprising cement, mortar, an admixture for concrete, an aggregate, a slurry or paste employed in forming a non-cementitious construction material;

providing the at least one self-contained sensor device of the plurality of self-contained sensor devices as part of a package of the second material for addition to the first predetermined portion of the construction material, wherein the second material is selected from the group comprising cement, mortar, an admixture for concrete, an aggregate, a slurry or paste employed in forming a non-cementious construction material, and a non-cementitious product employed in infrastructure construction; and providing the at least one self-contained sensor device of the plurality of self-contained sensor devices separately to the second material separately in response to an order for the second material, wherein the second material is selected from the group comprising cement, mortar, an admixture for concrete, an aggregate, a slurry or paste employed in forming a non-cementitious construction material, and a non-cementitious product employed in construction.

13. The method according to claim 8, further comprising: providing a bag which absorbs water through at least one of a natural process and being watered; wherein the bag is filled with the second material;

providing the second predetermined portion of the construction material comprises providing one of:

the at least one self-contained sensor device of the plurality of self-contained sensor devices as part of the bag where the second material is a cement or a mortar mix; and the at least one self-contained sensor device of the plurality of self-contained sensor devices as part of the bag and first predetermined portion of the first material where the first material is a concrete mix.

14. The method according to claim 8, wherein providing the second predetermined portion of the construction material comprises one of:

providing the at least one self-contained sensor device of a plurality of self-contained sensor devices mounted to a rebar;

providing the at least one self-contained sensor device of a plurality of self-contained sensor devices embedded within a formwork panel forming part of a framework within which the mixture of the first material is poured;

providing the at least one self-contained sensor device of a plurality of self-contained sensor devices mounted to formwork panel forming part of a framework onto which or into which the mixture of the first material is poured; and providing the at least one self-contained sensor device of a plurality of self-contained sensor devices in conjunction with a formwork panel such that the self-contained sensor device is in contact with the mixture of the first material, monitors the temperature of the mixture of the first material at one or more points, monitors the ambient temperature, and provides an indication upon determining that a strength of the mixture of the first material has reached a certain level, wherein the indication is selected from the group comprising a visual indication and a vibration.

15. The method according to claim 8, wherein
the microprocessor within each self-contained sensor device is further configured to:
   apply one or more scaling factors to the measured electrical resistivity of the first mixture; wherein
   a scaling factor of the one or more scaling factors a variation of electrical resistivity of the first mixture with water-to-cement ratio.

16. The method according to claim 8, further comprising an electronic device comprising at least a microprocessor and a wireless transceiver operating according to a predetermined wireless protocol, wherein the electronic device is configured to:
   wirelessly communicate with the at least one self-contained sensor device of a plurality of self-contained sensor devices to retrieve measurement data from the one or more sensors when embedded within the first material; and
   establish in dependence upon the retrieved measurement data and material data relating to the first mixture construction data relating to at least one of structural stability, a durability property, and a service life estimation of at least one of an element or structure formed from the first material.

17. A method comprising:
providing one or more sensors, each sensor comprising a microprocessor and one or more sensors in communication with the microprocessor;
providing a plurality of self-contained sensors, each self-contained sensor comprising another microprocessor, a battery, a memory in communication with the another microprocessor, a wireless interface and one or more other sensors in communication with the another microprocessor;
performing a plurality of measurements upon a mixture of a first material with the one or more sensors at a plurality of points in time; and
determining based upon at least the plurality of measurements obtained by the one or more sensors a pair of coefficients c and d which are mix dependent coefficients for determining an in-situ compressive strength (S) of the first material from one or more electrical resistivity ($\rho$) measurements of another mixture of the first material by one or more self-contained sensors embedded within the another mixture of the first material; and wirelessly transmitting the pair of coefficients c and d to each self-contained sensor of the plurality of self-contained sensors;
storing the pair of coefficients c and d within the memory forming part of each self-contained sensor of the plurality of self-contained sensors; wherein
the another microprocessor of each self-contained sensor of the plurality of self-contained sensors employs the pair of coefficients c and d upon the another microprocessor when executing a process to calculate the in-situ compressive strength (S) of the another mixture of the first material within which the self-contained sensor device is disposed.

18. The method according to claim 17, wherein
the in-situ compressive strength (S) of the mixture of the first material is established in dependence upon substituting a measured electrical resistivity ($\rho$) of the another mixture of the first material into the equation $S=c+d\cdot\log(\rho)$.

19. The method according to claim 17, wherein
the mix dependent coefficients c and d are established by:
   monitoring the electrical resistivity ($\rho$) of the mixture of the first material versus time;
   determining the electrical resistivity ($\rho_s$) of the mixture of the first material at which the concrete starts gaining strength (S=0);
   determining the electrical resistivity ($\rho_T$) and strength ($S_T$) of the mixture of the first material at a time (T) after the point where the mixture of the first material starts gaining strength; and
   solving for c and d with the following equations:

$$c/d=\log(\rho_s)$$

; and $$S_T=c+d\cdot\log(\rho_T).$$

20. The method according to claim 17, wherein
determining with the microprocessor an inflection point in the measured electrical resistivity ($\rho$) of the mixture of the first material versus time; wherein
the inflection point denotes a point in time that the mixture of the first material starts gaining strength.

21. The method according to claim 17, wherein
each self-contained sensor of the one or more self-contained sensors embedded within the another mixture of the first material comprises:
a plurality of sensors;
a first sensor of the plurality of sensors provides the one or more electrical resistivity ($\rho$) measurements; and
at least one of:
   a second sensor of the plurality of sensors is a pressure sensor allowing the depth at which the self-contained sensor device is deployed within the another mixture of the first material to be calculated in dependence upon a hydraulic pressure of the mixture of the first material;
   a plurality of third sensors of the plurality of sensors are temperature sensors disposed at different points internally or externally to the self-contained sensor device allowing a temperature gradient within the another mixture of the first material to be established; and
   a plurality of fourth sensors of the plurality sensors are humidity sensors disposed at different points internally or externally to the self-contained sensor device allowing a humidity gradient within the another mixture of the first material to be established.

\* \* \* \* \*